(12) United States Patent
Schaller et al.

(10) Patent No.: US 6,204,272 B1
(45) Date of Patent: Mar. 20, 2001

(54) USE OF AMINOTHIAZOLES FOR TREATING WOUNDS AND SKIN

(75) Inventors: Klaus Schaller, Wuppertal; Bernd Baasner, Bergisch Gladbach; Magdalena Liszkay; Hans-Otto Werling, both of Wuppertal; Ehrhardt Proksch, Molfsee, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/319,974

(22) PCT Filed: Jan. 7, 1998

(86) PCT No.: PCT/EP98/00033

§ 371 Date: Aug. 10, 1999

§ 102(e) Date: Aug. 10, 1999

(87) PCT Pub. No.: WO98/30212

PCT Pub. Date: Jul. 16, 1998

(30) Foreign Application Priority Data

Jan. 13, 1997 (DE) .............................. 197 00 795

(51) Int. Cl.$^7$ .................................................. A61K 31/505

(52) U.S. Cl. ............................................. 514/275; 514/256

(58) Field of Search ..................... 514/370, 390, 514/265, 275; 546/209; 548/184, 186; 424/246

(56) References Cited

U.S. PATENT DOCUMENTS

| 4,956,370 | 9/1990 | Ippen et al. |
|---|---|---|
| 5,104,889 * | 4/1992 | Kanai et al. ........................ 514/370 |
| 5,856,347 * | 1/1999 | Hashiguchi et al. ................. 514/370 |

FOREIGN PATENT DOCUMENTS

| 38 36 167 | 10/1988 | (DE) . |
|---|---|---|
| 38 39 758 | 11/1988 | (DE) . |
| 38 36 161 | 4/1990 | (DE) . |
| 365915 | 5/1990 | (EP) . |
| 718296 | 6/1996 | (EP) . |

* cited by examiner

Primary Examiner—William R. A. Jarvis
Assistant Examiner—Vickie Y. Kim
(74) Attorney, Agent, or Firm—Norris, McLaughlin & Marcus, P.A.

(57) ABSTRACT

The invention relates to the use of substituted 2-aminothiazoles for promoting wound healing.

6 Claims, 1 Drawing Sheet

Repair of the permeability barrier of the skin

—□— Compound of the formula (1)    —○— Control

Acceleration of wound healing

—■— Compound of the formula (1)    --○-- Control
—▲— Compound of the formula (1)    --×-- Control

USE OF AMINOTHIAZOLES FOR TREATING WOUNDS AND SKIN

This application is 371 of PCT/EP98/00033 filed on Jan. 13, 1997.

BACKGROUND OF THE INVENTION

1. Field of the Invention

The invention relates to the use of substituted 2-aminothiazoles for improving wound healing, and to the use of these compounds for preparing corresponding medicaments.

2. Description of Related Art

From EP-0 365 915, it is already known that such compounds have antimicrobial, in particular strong antibacterial and antimycotic action.

SUMMARY OF THE INVENTION

Surprisingly, it has now been found that these compounds also bring about a considerable improvement in wound healing.

The invention therefore relates to the use of 2-aminothiazoles of the general formula (I).

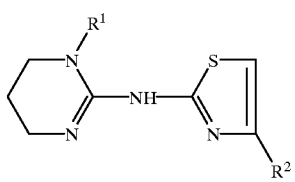

in which $R^1$ represents hydrogen or represents straight-cain or branched alkyl having 1 to 4 carbon atoms and $R^2$ represents a radical of the formula

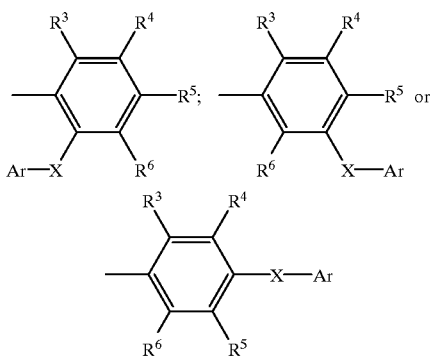

where $R^3$, $R^4$, $R^5$ and $R^6$ independently of one another each represent hydrogen, fluorine, chlorine, bromine, iodine, nitro, represent in each case straight-chain or branched alkyl, alkoxy, alkoxycarbonyl, dialkylamino, alkylthio, alkylsulphinyl or alkylsulphonyl having in each case 1 to 4 carbon atoms in the respective alkyl moieties or represent in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms—in particular fluorine, chlorine, bromine or iodine, X represents oxygen, sulphur, sulphinyl or sulphonyl and Ar represents phenyl, α-naphthyl, β-naphthyl, tetrahydronaphthyl or indanyl, each of which is optionally mono- or polysubstituted by identical or different substituents, possible substituents being in each case: fluorine, chlorine, bromine, iodine, in each case straight-chain or branched alkyl, alkoxy, alkoxycarbonyl, dialkylamino, alkylthio, alkylsulphinyl or alkylsulphonyl having in each case 1 to 8 carbon atoms in the respective alkyl moieties, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, cycloalkyl having 3 to 7 carbon atoms, phenylalkyl or phenoxyalkyl having in each case 1 to 4 carbon atoms in the straight-chain or branched alkyl moiety and also phenyl or phenoxy, and of their physiologically tolerable acid addition salts for improving wound healing.

BRIEF DESCRIPTION OF THE DRAWINGS

The invention will now be described in greater detail with reference to the drawings, wherein.

DETAILED DESCRIPTION OF THE INVENTION

Figure 1:
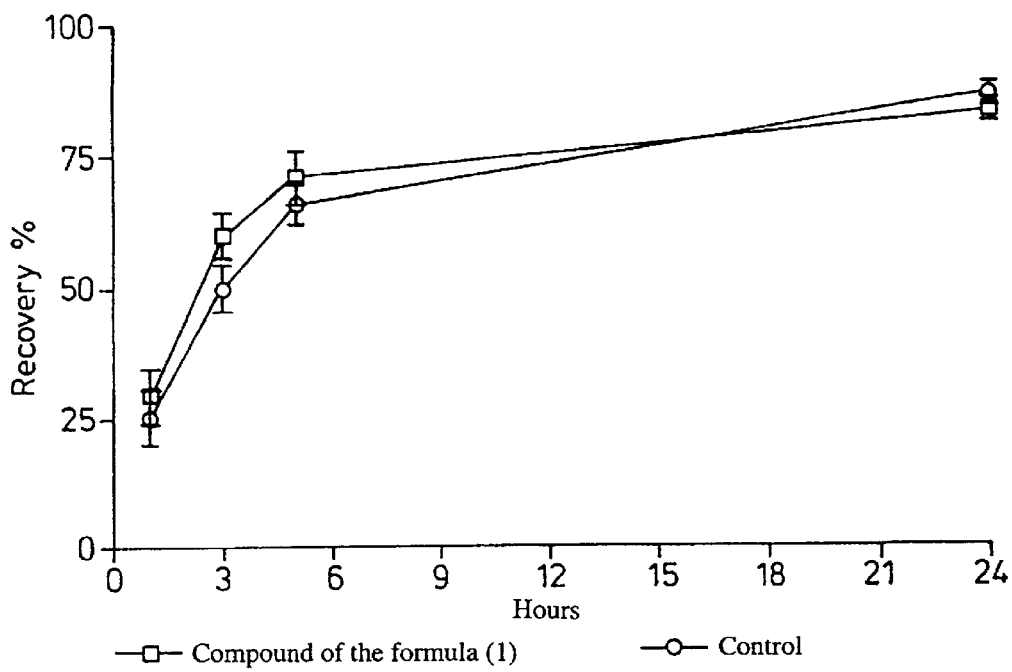
FIG. 1 is a graph depicting the repair of the permeability barrier of the skin as a function of time.

The compounds of the formula (I) are in equilibrium with the tautomeric compounds of the formulae (Ia) and (Ib),

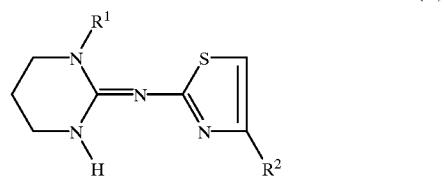

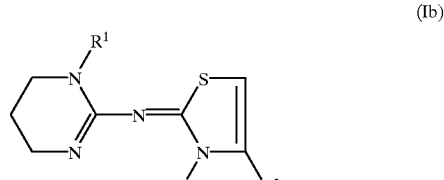

(where $R^1$ and $R^2$ are each as defined above) which are likewise claimed according to the invention.

A process for preparing the abovementioned compounds as described in EP-0 365 915.

The formula (I) provides a general definition of the 2-aminothiazoles substituted according to the invention. Preference is given to the use according to the invention of compounds of the formula (I) in which $R^1$ represents hydrogen, methyl or ethyl, and $R^2$ represents a radical of the formula

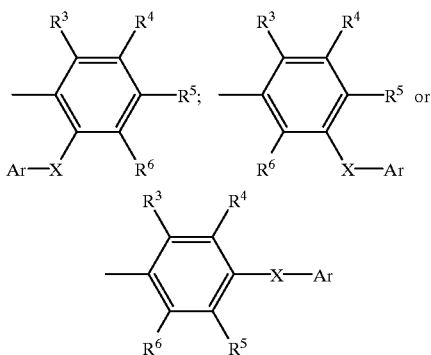

where
  $R^3$, $R^4$, $R^5$ and $R^6$ independently of one another each represent hydrogen, fluorine, chlorine, bromine, nitro, methyl, ethyl, methoxy, ethoxy, methoxycarbonyl, ethoxycarbonyl, dimethylamino, diethylamino, methylthio, ethylthio, methylsulphinyl, ethylsulphinyl, methylsulphonyl or ethylsulphonyl or represent halogenomethyl, halogenoethyl, halogenomethoxy, halogenoethoxy, halogenomethylthio, halogenoethylthio, halogenomethylsulphinyl, halogenoethylsulphinyl, halogenomethylsulphonyl or halogenoethylsulphonyl having in each case 1 to 5 identical or different halogen atoms, in particular fluorine, chlorine or bromine,
  X represents oxygen, sulphur, sulphinyl or sulphonyl and
  Ar represents phenyl, α-naphthyl, β-naphthyl, tetrahydronaphthyl or indanyl, each of which is optionally mono- to pentasubstituted by identical or different substituents, possible substituents being in each case: fluorine, chlorine, bromine, nitro, in each case straight-chain or branched alkyl, alkoxy, alkoxycarbonyl or dialkylamino having in each case 1 to 6 carbon atoms in the respective alkyl moieties, in each case straight-chain or branched alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in particular fluorine, chlorine or bromine, cyclohexyl having 3 to 6 carbon atoms, phenylalkyl or phenoxyalkyl having in each case 1 to 3 carbon atoms in the straight-chain alkyl moiety and also phenyl or phenoxy.

Particular preference is given to the use according to the invention of compounds of the formula (I) in which
  $R^1$ represents hydrogen or methyl and
  $R^2$ represents a radical

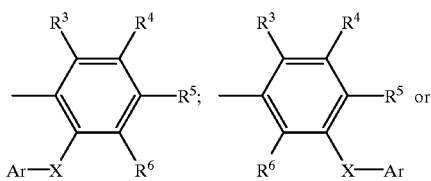

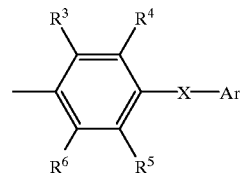

where
  $R^3$, $R^4$, $R^5$ and $R^6$ independently of one another each represent hydrogen, fluorine, chlorine, nitro, methyl, methoxy, ethoxycarbonyl, methoxycarbonyl, dimethylamino, methylthio, trifluoromethyl, trifluoromethoxy, trifluoromethylthio, trifluoromethylsulphinyl or trifluoromethylsulphonyl,
  X represents oxygen or sulphur and
  Ar represents phenyl, α-naphthyl, β-naphthyl, tetrahydronaphthyl or indanyl, each of which is optionally or mono- to tetrasubstituted by identical or different substituents, possible substituents being in each case: fluorine, chlorine, bromine, nitro, methyl, ethyl, n- or i-propyl, n-, i-, s- or t-butyl, methoxy, ethoxy, n- or i-propoxy, methoxycarbonyl, ethoxycarbonyl, dimethylamino, diethylamino, methylthio, ethylthio, methylsulphinyl, methylsulphonyl, trifluoromethyl, trifluoromethoxy, trifluoromethylthio, trifluoromethylsulphinyl, trifluoromethylsulphonyl, cyclopentyl, cyclohexyl, benzyl, phenylethyl, phenylpropyl, phenoxymethyl, phenyl or phenoxy.

Particularly preferred compounds are also the addition products of acids and those substituted 2-aminothiazoles of the formula (I) in which the substituents $R^1$ and $R^2$ have the meanings which have already been mentioned as being preferred for these substituents.

The acids which can be added preferably include hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, oxalic acid, maleic acid, malonic acid, succinic acid, fumaric acid, glutaric acid, hydroxyglutaric acid, adipic acid, oleic acid, tartaric acid, malic acid, citric acid, benzoic acid, salicylic acid, sorbic acid, and lactic acid, sulphonic acid, such as, for example, methanesulphonic acid, p-chlorobenzenesulphonic acid, p-toluenesulphonic acid and 1,5-naphthalenedisulphonic acid, sulphuric acid half-esters, such as sulphuric acid monomethyl ester or sulphuric acid monoethyl ester, and saccharin or thiosaccharin.

The especially preferred use according to the invention is that of compounds of the formula (I) in which
  $R^1$ represents hydrogen and
  $R^2$ represents a radical of the formula

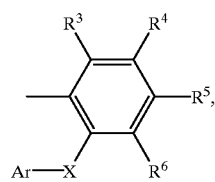

where
  $R^3$, $R^4$, $R^5$ and $R^6$ independently of one another each represent hydrogen, methyl, or nitro, X represents oxygen and Ar represents phenyl, which is optionally mono- to trisubstituted by identical or different substituents, possible substituents being, in particular: nitro, methyl, ethyl, n- or i-propyl, n-, i-, s- or t-butyl, methoxy, methylthio, cyclopentyl, cyclohexyl, phenyl or phenoxy.

The compounds of the formula (I) according to the invention and their acid addition salts have a pronounced favourable effect on the course of wound healing. In particular, wound healing and the repair of the permeability barrier of the skin are accelerated. They can therefore be employed for treating wounds and skin in humans and animals.

Examples which may be mentioned as indication examples in human medicine and veterinary medicine are therefore:

Assistance of wound healing and epithelisation, such as, for example, gangrene, abrasions and cuts, with chronic ulcers, decubitus and anal fissures. The compounds according to the invention can furthermore be used for aftertreatment in the case of skin grafts and surgical operations for cervical erosions. The compounds according to the invention are also suitable for prophylaxis and treatment of breast rhagades, as well as nappy erythemas and sunburn. Owing to their antimicrobial action, the compounds according to the invention can also be employed in the treatment of infected wounds.

The present invention includes pharmaceutical formulations such as are already described in EP 0 365 915, which comprise, in addition to non-toxic, inert pharmaceutically suitable excipients, one or more active compounds according to the invention or which consist of one or more active compounds according to the invention.

Pharmaceutical preparations (formulations) which are suitable for topical application are preferred.

The term "topical" as used in the present description relates to the use of the active constituent, which is processed with a suitable excipient material and applied to the skin or mucous membrane, so that it can display the local action. Accordingly, the topical medicaments include pharmaceutical dosage forms which are suitable for external use, so that direct contact with the skin results. The topical dosage forms include gels, creams, lotions, ointments, powders, aerosols and other conventional forms suitable for direct application of medicaments to the skin or mucous membrane.

The present invention also includes pharmaceutical preparations in dosage units. This means that the preparations are present in the form of individual components, for example suppositories and ampoules, the active compound content of which corresponds to a fraction or a multiple of an individual dose. The dosage units can comprise, for example, 1, 2, 3 or 4 individual doses or ½, ⅓ or ¼ of an individual dose. An individual dose preferably comprises the amount of effective compound which is administered in one application, and which usually corresponds to a whole or ½, ⅓ or ¼ of a daily dose.

Nontoxic, inert pharmaceutically suitable excipients are to be understood as solid, semi-solid or liquid diluents, fillers or formulating auxiliaries of all types.

Preferred pharmaceutical preparations which may be mentioned are granules, suppositories, solutions, suspensions and emulsions, pastes, ointments, gels, creams, lotions, powders or sprays.

Granules can comprise the active compound or compounds in addition to the customary excipients, such as (a) fillers and extenders, for example starches, lactose, sucrose, glucose, mannitol and silicic acid, (b) binders, for example, carboxymethylcellulose, alginates, gelatine or polyvinylpyrrolidone, (c) humectants, for example, glycerol, (d) disintegrants, for example agar-agar, calcium carbonate and sodium bicarbonate, (e) solution retarders, for example paraffin, and (f) absorption accelerators, for example quaternary ammonium compounds, (g) wetting agents, for example cetyl alcohol, glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The granules can be provided with the customary coverings and shells, which optionally comprise pacifying agents, and can be of a composition such that they release the active compound or compounds only or preferentially in a certain part of the intestinal tract, if appropriate in a delayed manner, it being possible, for example, to use the polymeric substances and waxes as embedding compositions.

The active compound or compounds can also be present in microencapsulated form, if appropriate with one or more of the abovementioned excipients.

Suppositories can comprise, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid), or mixtures of these substances.

Ointments, pastes, creams and gels can comprise, in addition to the active compound or compounds, the customary excipients, for example animal and vegetable fats, waxes, paraffins, starch, tragacanth, cellulose derivates, polyethylene glycols, silicones, bentonites, silicic acid, talc and zinc oxide, or mixtures of these substances.

Powders and sprays can comprise, in addition to the active compound or compounds, the customary excipients, for example lactose, talc, silicic acid, aluminium hydroxide, calcium silicate and polyamide powder, or mixtures of these substances. Sprays can additionally comprise the customary propellants, for example chlorofluorohydrocarbons.

Solutions and emulsions can comprise, in addition to the active compound or compounds, the customary excipients, such as solvents, solution retarders and emulsifiers, for example water, ethyl alcohol, isopropyl alcohol, acetone, ethyl carbonate, ethyl acetate, benzyl alcohol, benzyl benzoate, propylene glycol, 1,3-butyleneglycol, dimethylformamide, oils, in particular cotton seed oil, groundnut oil, maize germ oil, olive oil, caster oil and sesame oil, glycerol, glycerol formal, tetrahydrofurfuryl alcohol polyethylene glycols and fatty acid esters of sorbitan, or mixtures of these substances.

Suspensions can comprise, in addition to the active compound or compounds, the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminium metahydroxide, bentonite, agar-agar and tragacanth, or mixtures of these substances.

The abovementioned formulation forms can also comprise colorants, preservatives and additives which improve smell and taste, for example peppermint oil and eucalyptus oil, and sweeteners, for example saccharin.

The therapeutically active compounds should preferably be present in the abovementioned pharmaceutical preparations in a concentration of approximately 0.1 to 99%, preferably 0.5 to 95, % by weight of the total mixture.

Preparations for topical use can comprise, for example, 0.1 to 10% by weight, preferably 0.5 to 5% by weight, of therapeutically active compound, based on the total mixture. However, higher or lower concentrations can also be present, depending on the dosage form.

The abovementioned pharmaceutical preparations can also comprise further pharmaceutically active compounds, in addition to the active compounds according to the invention.

The abovementioned pharmaceutical preparations are produced in a customary manner by known methods, for example by mixing the active compound or compounds with the excipient or excipients.

The active compounds or the pharmaceutical formulations can be applied locally and/or rectally.

In general, it has proved advantageous both in human and in veterinary medicine to administer the active compound or compounds according to the invention in total amounts of approximately 2.5 to approximately 200, preferably from 5 to 150 mg/kg of body weight every 24 hours, if appropriate in the form of several individual doses, to achieve the desired results.

However, it may be necessary to deviate from the dosages mentioned, and in particular as a function of the nature and body weight of the subject to be treated, the nature and severity of the disease, the nature of the preparation and of the administration of the medicament, and of the period or interval within which administration takes place. Thus, in some cases, it may be sufficient to manage with less than the abovementioned amount of active compound, whereas in other cases the abovementioned amount of active compound has to be exceeded. The particular optimum dosage and mode of administration of the active compounds required can easily be specified by any expert on the basis of his expert knowledge.

EXAMPLES

A. Wound healing activity

The action of the compounds was tested in the following manner:

The repair of the permeability barrier of the skin and the acceleration of wound healing are investigated. The compound in question is applied in the form of a 1% strength solution in a solvent mixture comprising 50% by volume of acetone and 50% by volume of propylene glycol. As a control, for comparison, in each case the pure vehicle (50% by volume of acetone/50% by volume of propylene glycol) was applied.

a) Repair of the permeability barrier of the skin

The repair of the permeability barrier of the skin after artificial destruction of the barrier is investigated. To this end, hairless mice are treated with acetone, which is applied with a cotton swab, until an approximately 30-fold increase in the transepidermal water loss (TEWL) results. Immediately after destruction of the barrier, the substance in question or the vehicle (50% by volume of acetone/50% by volume of propylene glycol, 25 μl) is applied. 7 hairless mice are used in each group. In each case two measurement points are evaluated in the area treated. The barrier repair is measured after 1, 3, 5 and 24 hours.

Tests with the compound 4-[2-(2,4-dimethylphenoxy)-phenyl]-2-[2-(1,4,5,6-tetrahydropyrimidinyl)-amino]-thiazole of the formula (I)

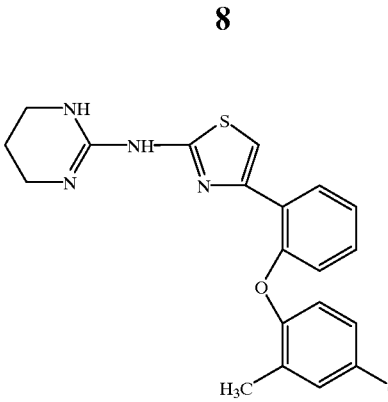

showed a significantly accelerated repair of the permeability barrier after 3 and 5 hours (see FIG. 1).

b) Acceleration of wound healing

Wound healing is investigated according to the procedure of Mellin et al. (Merck Research Laboratories, USA, J. Invest. Dermatol. 104 (1995), 850 to 855). To this end, a circular skin defect of a diameter of about 2 cm is brought about on diabetic hairless mice by excision of the entire skin. Directly afterwards (day 0) and on days 3 and 7, 25 μl of a solution of the compound in the abovementioned solvent are applied. For comparison, the pure solvent (vehicle) is also applied. The wounds are covered with a semipermeable film (Comfeel plus) for 18 days. The size of the wound is determined on days 0, 3, 7, 11, 15 and 18. The TEWL in former wound area is measured on days 22 and 25.

Tests with the abovementioned compound 4-[2-(2,4-dimethylphenoxy)-phenyl]-2-[2-(1,4,5,6-tetrahydropyrimidinyl)-amino]-tiazole of the formula (1)

Figure 2:
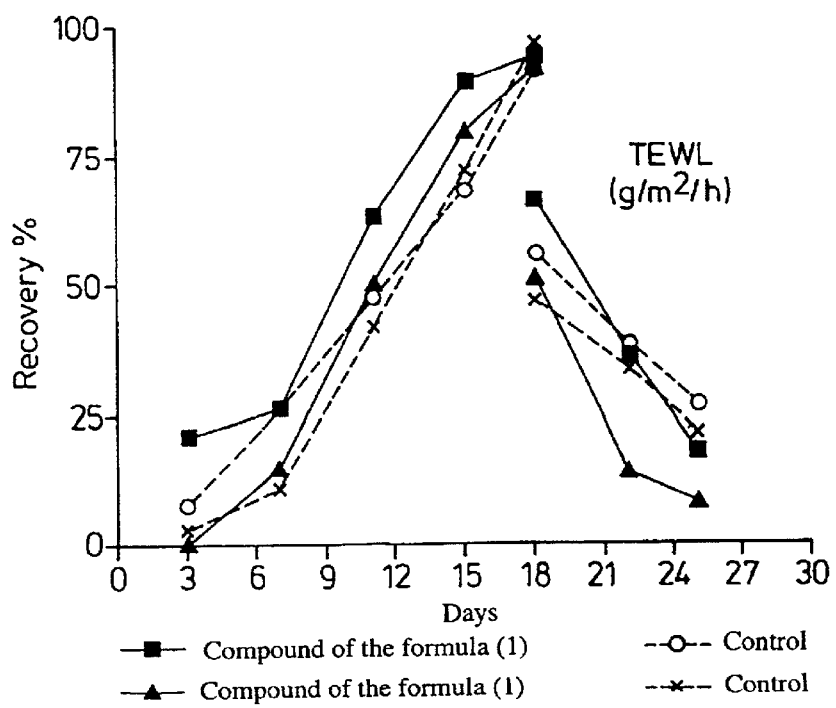
FIG. 2 is a graph depicting the acceleration of wound healing also as a function of time.

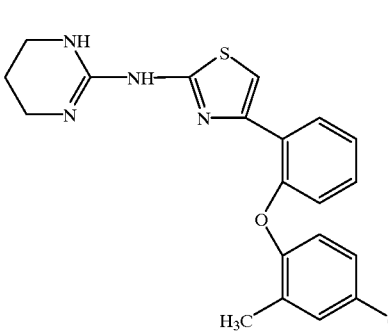

showed a significantly accelerated wound healing (see FIG. 2).

B. Formulation examples

Solution formulation 1 g of the compound of the formula (1) is dissolved in 99 g of a solvent mixture of 50% by volume of acetone and 50% by volume of propylene glycol, while stirring.

What is claimed is:

1. A method for improving the wound healing of a patient in need thereof, which comprises administering to said patient, an effective amount therefor of a 2-aminothiazole of the formula (I)

(I)

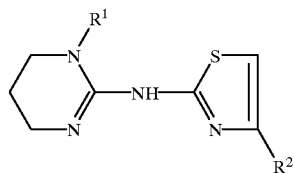

in which

R¹ represents hydrogen or represents straight-chain or branched alkyl having 1 to 4 carbon atoms and R² represents a radical of the formula

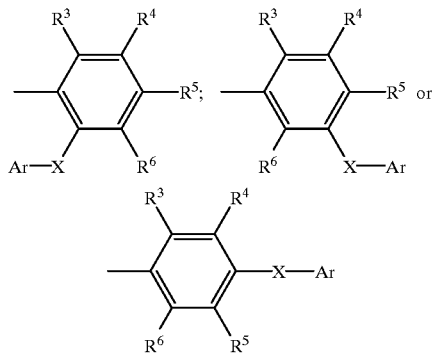

where

R³, R⁴, R⁵ and R⁶ independently of one another each represent hydrogen, fluorine, chlorine, bromine, iodine, nitro, represent in each case straight-chain or branched alkyl, alkoxy, alkoxycarbonyl, dialkylamino, alkylthio, alkylsulphinyl or alkylsulphonyl having in each case 1 to 4 carbon atoms in the respective alkyl moieties or represent in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms X represents oxygen, sulphur, sulphinyl or sulphonyl and Ar represents phenyl, α-naphthyl, β-naphthyl, tetrahydronaphthyl or indanyl, each of which is optionally mono- or polysubstituted by identical or different substituents, the substituents being in each case: fluorine, chlorine, bromine, iodine, in each case straight-chain or branched alkyl, alkoxy, alkoxycarbonyl, dialkylamino, alkylthio, alkylsulphinyl or alkylsulphonyl having in each caase 1 to 8 carbon atoms in the respective alkyl moieties, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, cycloalkyl having 3 to 7 carbon atoms, phenylalkyl or phenoxyalkyl having in each case 1 to 4 carbon atoms in the straight-chain or branched alkyl moiety and also phenyl or phenoxy, or a physiologically tolerable acid addition salt thereof.

2. Method according to claim 1, wherein compounds of the formula (I) are administered in which R¹ represents hydrogen, methyl or ethyl, and R² represents a radical of the formula

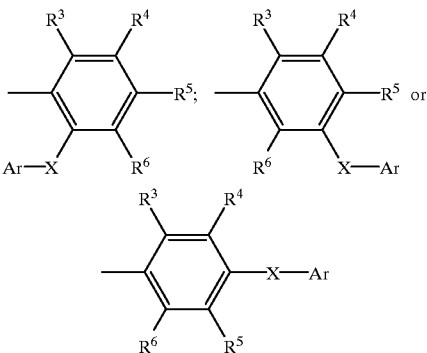

where

R³, R⁴, R⁵ and R⁶ independently of one another each represent hydrogen, fluorine, chlorine, bromine, nitro, methyl, ethyl, methoxy, ethoxy, methoxycarbonyl, ethoxycarbonyl, dimethylamino, diethylamino, methylthio, ethylthio, methylsulphinyl, ethylsulphinyl, methylsulphonyl or ethylsulphonyl or represent halogenomethyl, halogenoethyl, halogenomethoxy, halogenoethoxy, halogenomethylthio, halogenoethylthio, halogenomethylsulphinyl, halogenoethylsulphinyl, halogenomethylsulphonyl or halogenoethylsulphonyl having in each case 1 to 5 identical or different halogen atoms, X represents oxygen, sulphur, sulphinyl or sulphonyl and Ar represents phenyl, α-naphthyl, β-naphthyl, tetrahydronaphthyl or indanyl, each of which is optionally mono- to pentasubstituted by identical or different substituents, the substituents being in each case: fluorine, chlorine, bromine, nitro, in each case straight-chain or branched alkyl, alkoxy, alkoxycarbonyl or dialkylamino having in each case 1 to 6 carbon atoms in the respective alkyl moieties, in each case straight-chain or branched alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in particular fluorine, chlorine or bromine, cyclohexyl having 3 to 6 carbon atoms, phenylalkyl or phenoxyalkyl having in each case 1 to 3 carbon atoms in the straight-chain alkyl moiety and also phenyl or phenoxy.

3. Method according to claim 1, wherein compounds of the formula (I) are administered in which R¹ represents hydrogen or methyl and R² represents a radical

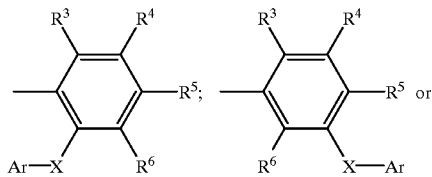

-continued

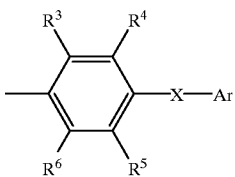

where
R³, R⁴, R⁵ and R⁶ independently of one another each represent hydrogen, fluorine, chlorine, nitro, methyl, methoxy, ethoxycarbonyl, methoxycarbonyl, dimethylamino, methylthio, trifluoromethyl, trifluoromethoxy, trifluoromethylthio, trifluoromethylsulphinyl or trifluoromethylsulphonyl, X represents oxygen or sulphur and Ar represents phenyl, α-naphthyl, β-naphthyl, tetrahydronaphthyl or indanyl, each of which is optionally or mono- to tetrasubstituted by identical or different substituents, the substituents being in each case: fluorine, chlorine, bromine, nitro, methyl, ethyl, n- or i-propyl, n-, i-, s- or t-butyl, methoxy, ethoxy, n- or i-propoxy, methoxycarbonyl, ethoxycarbonyl, dimethylamino, diethylamino, methylthio, ethylthio, methylsulphinyl, methylsulphonyl, trifluoromethyl, trifluoromethoxy, trifluoromethylthio, trifluoromethylsulphinyl, trifluoromethylsulphonyl, cyclopentyl, cyclohexyl, benzyl, phenylethyl, phenylpropyl, phenoxymethyl, phenyl or phenoxy.

4. Method according to claim 1, wherein compounds of the formula (I) are administered in which R¹ represents hydrogen and R² represents a radical of the formula

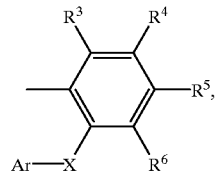

where
R³, R⁴, R⁵ and R⁶ independently of one another each represent hydrogen, methyl or nitro, X represents oxygen and Ar represents phenyl, which is optionally mono- to trisubstituted by identical or different substituents, the substituents being: nitro, methyl, ethyl, n- or i-propyl, n-, i-, s- or t-butyl, methoxy, methylthio, cyclopentyl, cyclohexyl, phenyl or phenoxy.

5. The method of claim 1, wherein said 2-aminothiazole is administered by applying topically.

6. The method of claim 1, wherein said 2-aminothiazole is administered rectally.

* * * * *